United States Patent
Sawa

[11] Patent Number: 5,951,288
[45] Date of Patent: Sep. 14, 1999

[54] SELF EXPANDING DENTAL IMPLANT AND METHOD FOR USING THE SAME

[76] Inventor: Shlaimon T. Sawa, 6849 N. Sauganash Ave., Chicago, Ill. 60646

[21] Appl. No.: 09/111,135

[22] Filed: Jul. 3, 1998

[51] Int. Cl.$^6$ ........................................................ A61C 8/00
[52] U.S. Cl. ........................ 433/173; 433/175; 433/201.1
[58] Field of Search ................................. 433/173, 201.1, 433/172, 174, 175, 176

[56] References Cited

U.S. PATENT DOCUMENTS

| | | | |
|---|---|---|---|
| 3,082,525 | 3/1963 | Christensen | 433/174 |
| 4,011,602 | 3/1977 | Rybicki et al. | 433/173 |
| 4,468,201 | 8/1984 | Fukuyo | 433/176 |
| 4,609,354 | 9/1986 | Koch | 433/173 |
| 4,832,601 | 5/1989 | Linden | 433/173 |
| 5,009,596 | 4/1991 | Soderberg | 433/173 |
| 5,219,287 | 6/1993 | Nishihara | 433/201.1 |
| 5,344,318 | 9/1994 | Wilson et al. | 433/169 |
| 5,470,230 | 11/1995 | Daftary et al. | 433/174 |
| 5,489,210 | 2/1996 | Hanosh | 433/173 |
| 5,697,779 | 12/1997 | Sachdeva et al. | 433/173 |
| 5,810,592 | 9/1998 | Daftary | 433/173 |

Primary Examiner—John J. Wilson
Assistant Examiner—Patrick A. Hilsmier
Attorney, Agent, or Firm—Meroni & Meroni

[57] ABSTRACT

The present invention is a dental implant inserted into the jaw bone for anchoring an artificial tooth in the bone. It has been designed to overcome the difficulties and complexities of prior art implants. The inventive implant consists of three simple components: An elongate body which has an neck portion and a root portion; an abutment which is mounted to the neck portion of the body and which receives the temporary or permanent replacement tooth; and a screw which secures the abutment to the body. The root portion of the body consists of multiple legs and is formed from a shape memory alloy. Use of shape memory alloy allows the root portion to assume a closed, elongate shape at cool temperatures and to assume an open, fanned shape at temperatures typical of the human body. The inventive implant is maintained at cool temperatures until and during insertion into the body allowing an easy and non-traumatic placement of the implant. Once in place, the implant warms to body temperature and self expands to anchor itself within surgical site. A method for using this self-expanding dental implant is also provided.

44 Claims, 6 Drawing Sheets

SELF EXPANDING DENTAL IMPLANT AND METHOD FOR USING THE SAME

BACKGROUND OF THE INVENTION

The present invention relates to dental implants which are surgically placed in the bone of the jaw to provide an anchoring means for an artificial tooth. Specifically, the present invention is a dental implant which employs shape memory material in the lower portions of the implant to provide self expanding legs, resulting in instantaneous implant stability.

Numerous dental implants found are found in the prior art. Pertinent prior patents are summarized as follows:

U.S. Pat. No. 2,721,387 to Ashuckian discloses an implant having multiple expandable legs. The legs are expanded relative to a spring action apex which is located at the lowermost edge of the implant. Aushuckian also discloses a second embodiment wherein the leg portions are mechanically spread apart using a spreading means between the legs.

U.S. Pat. No. 3,708,883 to Flander discloses an implant having two legs which are mechanically spread apart using wedging means between the legs. Flander does not disclose the use of temperature dependent material to change the relative positions of the legs. Flander also employs the use of exterior projections on the outer surfaces of the legs which are intended to engage the bone. If not completely engaged with the bone, these projections provide gaps between the bone and the legs, allowing encapsulation of the legs by fibrous tissue and preventing osseointegration.

U.S. Pat. No. 4,609,354 to Koch discloses an implant for securing a tooth replacement which uses a shaft implanted in the jaw bone. The shaft has a bore which receives a peg, the peg being the structure which supports an artificial tooth. The diameter of the peg is temperature dependent so that at body temperature the peg diameter is maximized, thus maintaining the peg within the bore. By cooling the peg, the peg can be removed from the shaft. Koch uses a temperature-dependent material to attach different structural portions of the implant to each other. The temperature dependent material is not related to anchoring the dental implant within the jaw.

U.S. Pat. No. 4,832,601 to Linden discloses an implant comprising an upper portion which is pivotably adjustable. The lower portion of the implant is secured within the jaw bone using multiple shingle-shaped members which project into the jaw bone. The projecting members extend from a single shaft and do not appear to be adjustable. Further, Linden does not disclose the use of temperature dependent materials to anchor the implant within the jaw bone.

U.S. Pat. No. 5,219,287 to Nishihara discloses an artificial dental root formed of a shape memory alloy. The implant changes shape upon contact with body heat to engage the jaw bone. There are two disadvantages to using this implant. First, the entire implant is made from the shape memory alloy. Thus, the portion of the implant which extends above the jaw to receive the artificial tooth will be affected and changed each time the patient consumes something hot or cold. Secondly, the curved and branched shape of the root portion provides gaps and spaces between the root and jaw bone. Such spaces provide opportunity for encapsulation by fibrous tissue, preventing osseointegration.

SUMMARY OF THE INVENTION

To achieve a successful dental implant, the dental implant must be highly stable within the jaw, both initially and over the long term. Obviously, a stable dental implant allows the patient to use the artificial tooth comfortably and securely. However, stable implantation is also key to long term avoidance of failure of the dental implant. This is because stability of the dental implant is essential for the growth of the bone around the dental implant. Such growth, called osseointegration, occurs around and in the vicinity of a stable dental implant and provides a strong, fixed means of securing the dental implant in the body. Conversely, studies have shown a positive correlation between an unstable or mobile dental implant and formation of connective tissue in the peri-implant space. Formation of connective tissue around the dental implant prevents osseointegration, thus insuring failure of the dental implant.

Studies have shown that compression forces in bone initiates and stimulates bone formation by increasing growth of plate cartilage[1], and further shows that osteoclastic activity, or bone absorption or break down, is reduced or inhibited by mechanical stimulation or pressure[2].

[1]"Increased Calcification of Growth Plate Cartilage as a Result of Compressive Force In Vitro," J. Klein-Nulend, J. P. Veldhuijzen, and E. H. Burger. *Arthritis & Rheumatism*, Vol. 29 (8), 1002–1009, 1986.

[2]"Inhibition of Osteoclastic Bone Resorption by Mechanical Stimulation In Vitro," J. Klein-Nulend, J. P. Veldhuijzen, M. E. Van Strien, M. De Jong, and E. H. Burger. *Arthritis & Rheumatism*, Vol. 33 (1), 66–72, 1990

The present invention is a dental implant inserted into the jaw bone as a means for anchoring an artificial tooth in the bone. It has been designed to overcome the difficulties and complexities of prior art implants. The inventive implant consists of three components: An elongate body which has an neck portion and a root portion; an abutment which is mounted to the neck portion of the body and which receives the temporary or permanent replacement tooth; and a screw which secures the abutment to the body. The root portion of the body consists of multiple legs and is formed from a shape memory alloy. Use of shape memory alloy allows the root portion to assume a closed, elongate shape at cool temperatures and to assume an open, fanned shape at temperatures typical of the human body. The inventive implant is maintained at cool temperatures until and during insertion into the body allowing an easy and non-traumatic placement of the implant. Once in place, the implant warms to body temperature and self expands to anchor itself within surgical site.

Use of shape memory material in the lower portions of the implant is an important feature because the practitioner is not required to manipulate the implant into an expanded position once it has been placed in the body, and further eliminates the need for additional, perhaps specialized, tools.

The design of the implant and its method of use provides an implant which expands in the surgical site, producing compressive stresses on the surrounding bone tissue. This has three important consequences. First, the implant is immediately stabilized within the jaw. Second, since the implant is compressed into the bone material, formation of connective tissue around the implant is prevented. Third, osseointegration is promoted about the implant which insures long term success of the implant.

Because the inventive dental implant consists of only three components, and because these components are simple in design, the inventive dental implant will be less costly to manufacture than other, more complex dental implants. Cost of the dental implant is an important consideration for both the practitioner and the patient. Reductions in cost will remove an economic barrier to many millions of people who are candidates for tooth replacement procedures.

The simple design employed by the inventive dental implant reduces the time and cost required by the practitioner to understand the function of the implant and to learn and master the surgical techniques required for a successful implantation. The inventive dental implant is easy to use, requires no manipulation once it has been placed in the jaw, and requires no special tools for placement.

The inventive dental implant prevents bacterial invasion from the oral environment to the bone by using design features which prevent direct communication between the oral environment and the bone. A bacterial infection of the bone in the vicinity of the implant can lead to failure of the implant. The inventive dental implant does not provide a passageway between the oral environment and the bone, thus sealing the implant site against bacterial invasion. Additionally, the inventive dental implant employs smooth, uniform exterior surfaces to reduce the likelihood of bacterial growth.

The inventive dental implant is manufactured in a predetermined expanded shape. The implant is then cooled to reform the implant into a contracted shape which is a generally elongate cylinder. In this form, the implant is ready for insertion into the jaw bone of a patient.

A second embodiment of the inventive dental implant is provided. The second embodiment is identical to the first with the exception of an axial passageway which is formed through the body portion of the implant. This passageway allows the practitioner to insert bone fragments through the implant for placement within the space between the opened legs. By packing this space with bone fragments, implant stability and osseointegration are improved even more.

Method steps for insertion of the implant into the jaw bone of an animal are provided. These method steps are inventive because of the unique nature of the implant and also because of the elimination of the complex series of steps required to manipulate the prior art implants. In the inventive method, fewer drilling steps are required than are required by the prior art implants. Fewer tools are employed since bone taps and actuating tools are not required in the inventive method.

DETAILED DESCRIPTION

Figure 1:
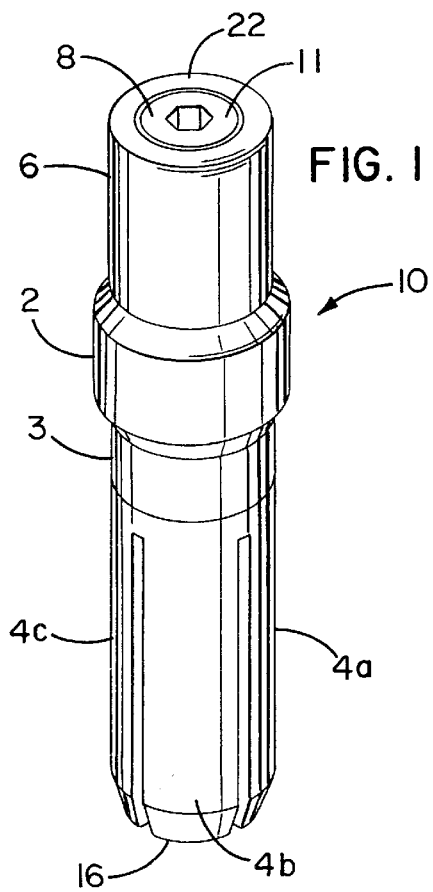
FIG. 1 is a side perspective view of the first embodiment of the implant showing the legs in a closed position.
Figure 2:
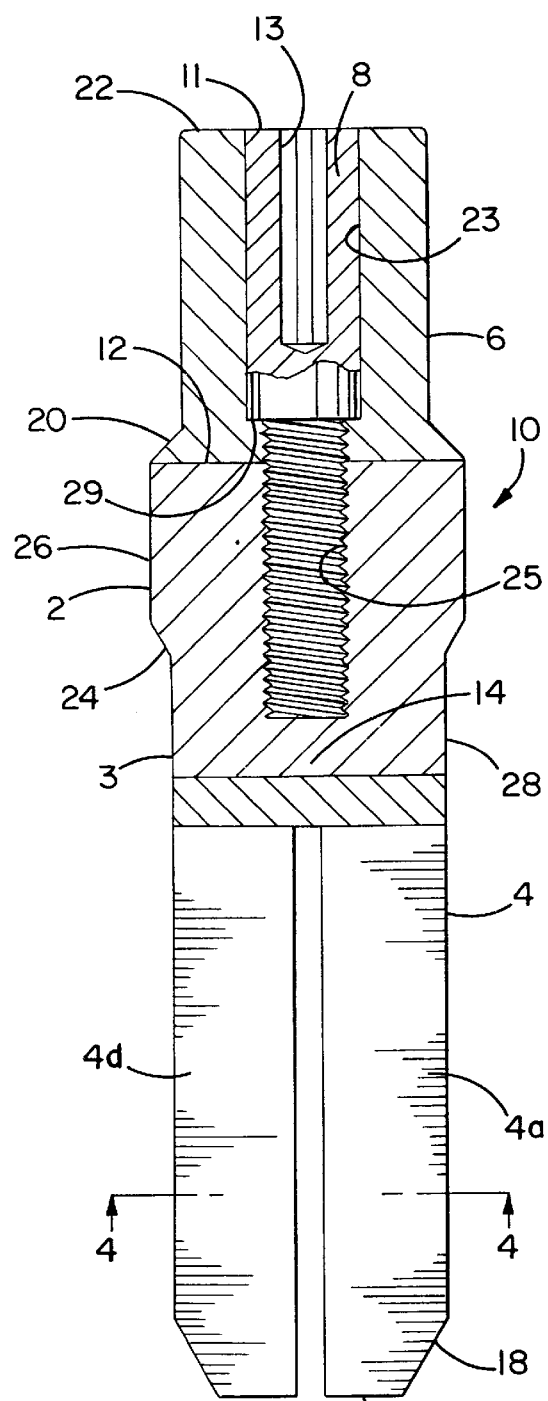
FIG. 2 is a side sectional view of the first embodiment of the implant showing the legs in a closed position.

Referring now to the drawings, the preferred embodiment of the dental implant is shown in FIGS. 1–5. Dental implant 10 has three components. These components are the body 3, the abutment 6, and the screw 8. The screw 8 is used to secure the abutment 6 to the upper end 27 of the body 3.

The body 3 is an elongate cylinder having an upper portion or neck 2, a mid portion or apex 14, and a lower portion or legs 4. The body 3 is uniform in diameter except at the neck 2, which has a slightly larger diameter than the apex 14 and legs 4. A first chamfer 24 is formed on the exterior of the body 3 at the transition between the neck 2 and apex 14. The body 3 has an axial channel 25 which extends from the upper end 27 of the body 3 through the neck 2 and terminates adjacent the apex 14. Channel 25 is threaded and is sized to receive the threads of the shank 7 of screw 8.

At least two legs 4A, 4B, extend from the apex 14. In the preferred embodiment, there are four legs 4A, 4B, 4C, 4D, extending from the apex 14 of the body 3 but variations in the number of legs 4 are within the scope of this invention to accommodate the specific requirements of a given application.

Figure 4:
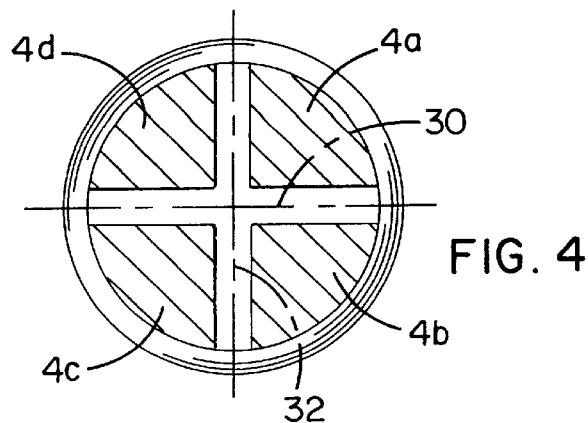
FIG. 4 is a sectional view of the leg portion of the implant taken across line 4—4 in FIG. 2.

In the preferred embodiment, the legs 4 are formed in the elongate cylinder by making two longitudinal cuts through the lower portion of the cylinder. Referring to FIG. 4, a first cut is made along a first transverse axis 30 which bisects the cross section of the body 3. A second cut is made along a second transverse axis 32 which is perpendicular to the first axis 30 and also bisects the cross section of the body 3. Each of the legs 4 has a first end which extends from apex 14, and a second end 16 which is opposed to the first end and provides the leading edge during implant 10 insertion into the jaw bone. The peripheral edge 18 of the second end 16 of each leg 4 is rounded to ease insertion of the implant 10.

Figure 3:
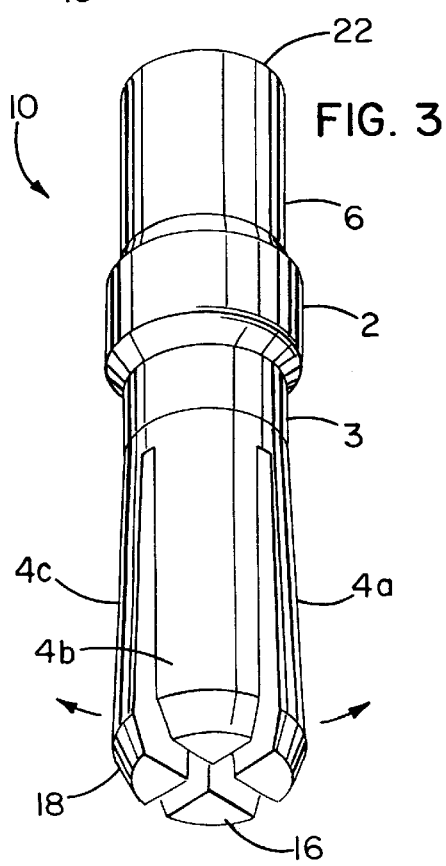
FIG. 3 is a side perspective view of the first embodiment of the implant showing the legs in an open position.

The legs 4 can assume two different positions. The first position is shown in FIG. 1, where the legs 4 are lying a closed position such that the legs are lying parallel to each other and the second ends 16 of the legs 4 are closely adjacent to each other. The second position is shown in FIG. 3 which shows the second ends 16 of the legs 4 spaced apart. In this position the legs 4 are no longer parallel but instead intersect at apex 14 and fan out therefrom.

Figure 5:
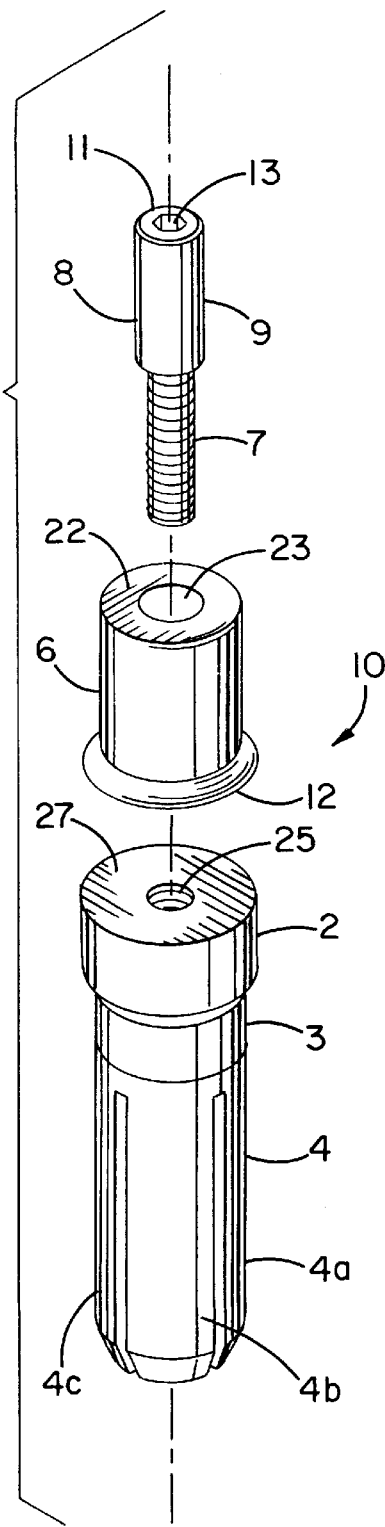
FIG. 5 is an exploded side perspective view of the implant.
Figure 7:
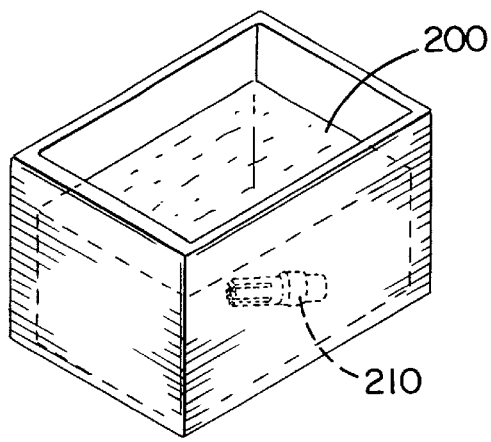
FIG. 7 illustrates the first step of the method of using the implant, showing the implant maintained in a cold water bath prior to insertion in the jaw.

The abutment 6 is attached to the upper edge of the neck 2 by means of screw 8 (FIG. 5). The abutment is an elongate hollow cylinder having an upper end 22 and a lower end 12. The exterior surface of the abutment is smooth and uniform except at the. lower end 12. Lower end 12 terminates in a second chamfer 20 which widens the diameter of the abutment 6 to the diameter of the neck 2 of the body 3. The interior channel 23 of the abutment 6 is smooth and uniform except at the lower end 12 where an inwardly extending lip 29 is formed. Channel 23 is sized to receive the head 9 of the screw 8.

Screw 8 has an elongate head 9 such that the upper end 11 of the screw 8 lies generally flush with the upper end 22 of the abutment. A hexagonally shaped recess 13 extends from upper end 11 to provide a means of manipulating the screw 8. Recess 13 extends generally through the length of the head 9, terminating within the head 9. A threaded shank 7 extends from the head 9 and is received in channel 25 of body 3. The threads of the shank 7 are sized to engage the threaded interior surface of channel 25.

The legs 4 and apex 14 of the implant 10 are formed from a shape memory alloy. The properties of the shape memory alloy allow the implant 10 to assume one shape at a low temperature and to assume a second shape at a higher temperature. The implant 10 of the current invention is designed to assume the first, or closed, position when the implant 10 is placed in an environment which is much colder than the human body. When the implant 10 is raised to body temperature, the implant 10 self expands to the second, or open, position. In the preferred embodiment, the shape memory alloy used will be a Nickel-Titanium (NiTi) Alloy. However, other shape memory alloys such as, but not limited to, Titanium-Palladium (TiPd) or Titanium-Palladium-Cobalt (TiPd-Co) can be used to achieve the desired positioning effect.

The remaining portions of the implant 10 are not formed from shape memory alloy. These portions of the implant are at the jaw line or extend above it during use and are thus exposed to a broad range of temperatures as the patient consumes food and beverages. To avoid shape changes in the upper portions of the implant, the remaining portions are formed from materials which are biocompatible but are not affected by temperature. In the preferred embodiment, the neck portion is made from a Titanium alloy such as Titanium (90 percent), Venedium (4 percent) and Aluminum (6 percent). The abutment 6 and screw 8 are made from Titanium or Gold.

Implant 10 will be provided in four lengths to accommodate placement at various locations within an adult mouth. In the preferred embodiment, the abutment 6 will have a diameter of 3.5 mm and a length of 10 mm. The neck 2 will have a diameter of 4.5 mm and a length of 2 mm. The apex will have a diameter of 4 mm and a length of 2 mm. The legs 4 will have a 4 mm outer diameter and will be provided in 5 mm, 8 mm, 11 mm and 13 mm lengths. At maximum expansion, the outer diameter of the second ends 16 of the legs 4 will be approximately 8 mm.

It should be noted that it is within the scope of this invention that the dimensions of the implant 10 can be increased or decreased to accommodate the requirements of a specific application. It is further within the scope of this invention to change the dimensions of the implant to accommodate the jaw bone of a juvenile mouth, or the mouth of an animal other than a human being.

Figure 6:
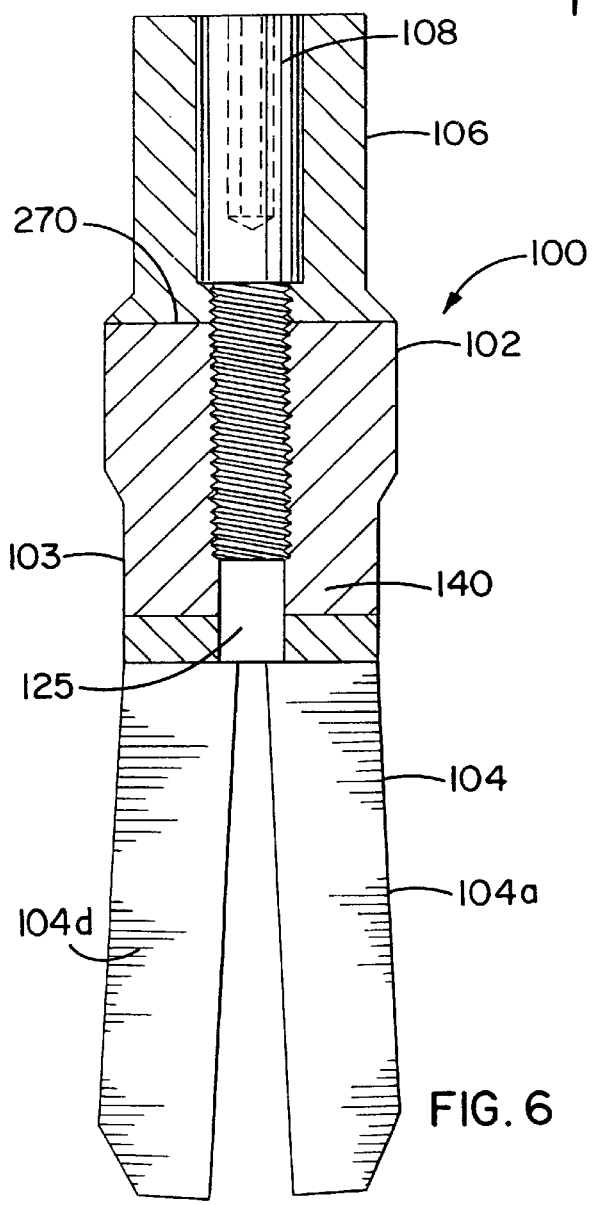
FIG. 6 is a side sectional view of the second embodiment of the implant showing the legs in an open position.

A second embodiment of the inventive implant is shown in FIG. 6. Dental implant 100 has three components: the body 103, the abutment 106, and the screw 108, where screw 108 is used to secure the abutment 106 to the upper end 270 of the body 103.

The body 103 is an elongate cylinder having an upper portion or neck 102, a mid portion or apex 140, and a lower portion or legs 104. The body 103 is uniform in diameter except at the neck 102, which has a slightly larger diameter than the apex 140 and legs 104. The body 103 has an axial channel 125 which extends from the upper end 270 of the body 103 through the neck 102 and apex 140 and exits the body 103 between the legs 104. Channel 125 is threaded from the upper end 270 to the apex 140, and is smooth and uniform between the apex 140 and the legs 104. The threaded portion of channel 125 is sized to receive the threads of the shank 107 of screw 108.

The shape and function of implant 100 is identical to that of implant 10 with the exception of channel 125. Channel 125 extends completely through the body 103 to form a passageway. The passageway is used, after implantation in the jaw bone, to allow insertion of bone fragments into the space between the opened legs 104. Once the space has been packed with bone fragments, the screw 108 is engaged with the threaded portion of channel 125. Screw 108 is used to secure the abutment 106 to the body 103 and also is a means by which the channel 125 is sealed to prevent bacterial transfer from the oral environment to the jaw bone.

Method of Use

A method of using the implant 10 will now be described with reference to FIGS. 7–16.

The implant 210 is provided with legs in the closed position by maintaining the implant in a cold environment. This is achieved by immersion of the implant 210 in a cold water bath 200 (FIG. 7), or by any other suitable means.

Figure 8:
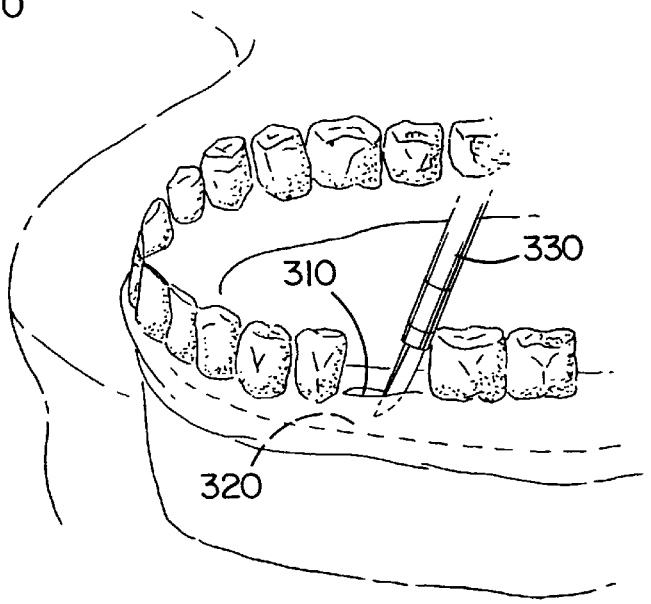
FIG. 8 illustrates a subsequent step of the method of using the implant, showing an incision being formed in the gum to expose the jaw bone.

The surgical site, or osteotome is prepared by making an incision 310 in the gum 300 at the desired location to expose the jaw bone 320 (FIG.8).

Figure 9:
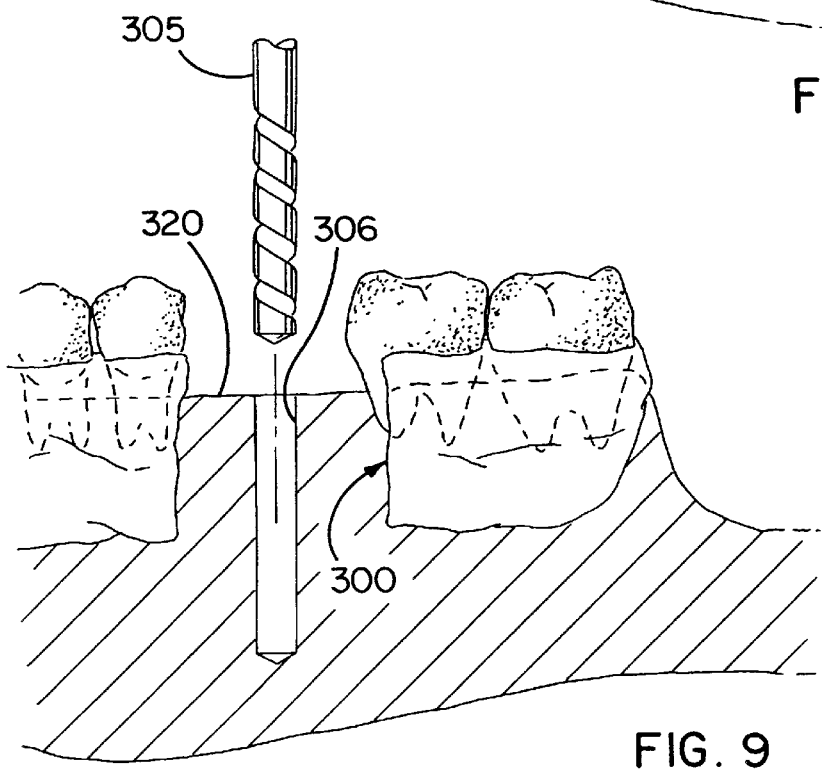
FIG. 9 illustrates a subsequent step of the method of using the implant, showing the initial small drill hole.
Figure 10:
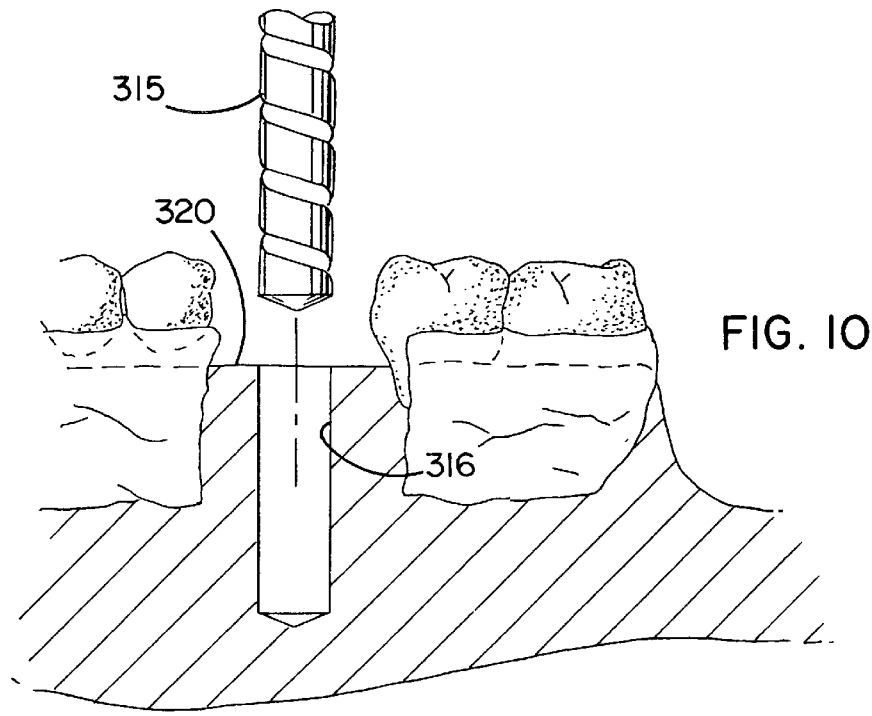
FIG. 10 illustrates a subsequent step of the method of using the implant, showing the final drill hole.
Figure 11:
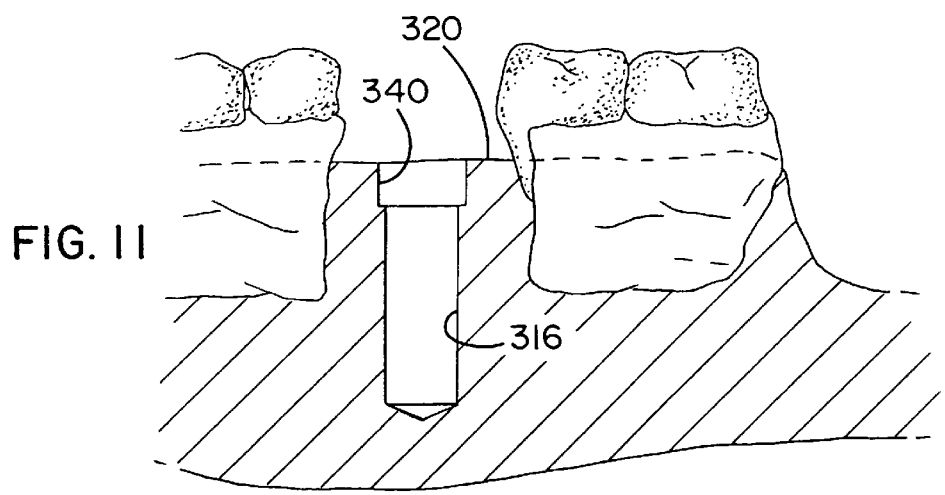
FIG. 11 illustrates a subsequent step of the method of using the implant, showing the counter bore in the upper end of the drill hole.

An implant-receiving hole 316 is formed in the jaw bone 320 using a series of drills. Concurrent with each of the drilling steps, a continuous cold water wash is provided over the surgical site to prevent tissue damage resulting from friction induced high temperatures in the jaw bone 320 and surrounding tissues 300. An initial drill 305 is used to form a small diameter hole 306 to verify implant location and direction within the jaw bone 320 (FIG. 9). A second drill 315, having a larger diameter than the initial drill 305 and having the same diameter as the outer diameter of the leg portion of the implant 210, is used to enlarge the hole 316 to final diameter and depth (FIG. 10). A counter-bore drill is then used to enlarge the upper portion 340 of the implant-receiving hole 316 (FIG. 11). The upper portion 340 of hole 316 is sized to receive the neck portion of the implant 210 in a fitted, supporting relationship.

Figure 12:
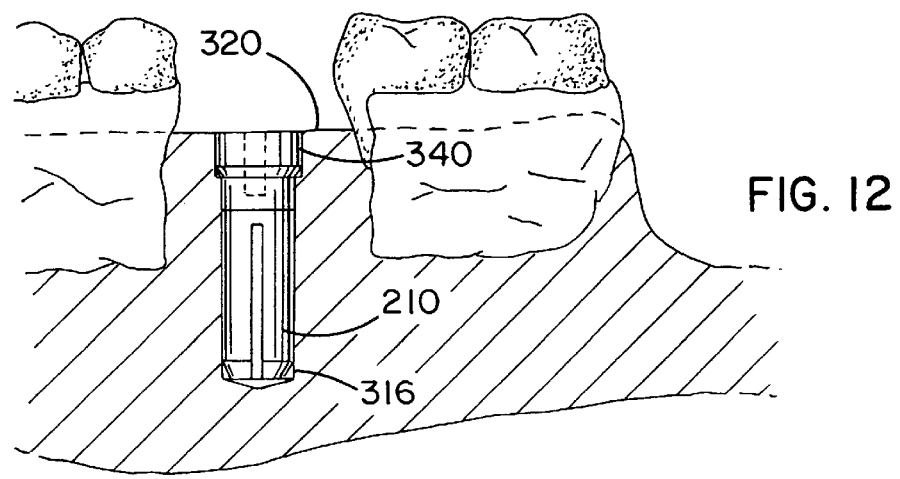
FIG. 12 illustrates a subsequent step of the method of using the implant, showing insertion of the implant into the drill hole so that the legs reside within the hole and the neck portion resides in the counter bored portion of the drill hole.

The implant 210 is positioned in the implant receiving hole 316 by inserting it legs-first in hole 316 so that the legs are completely contained within the hole 316 and the neck portion is fitted into the widened upper portion 340 of the hole 316 (FIG. 12). The cold water wash is continued during the insertion step to prevent premature expansion of the legs.

The cold water wash is discontinued to allow the surgical site to return to normal body temperature.

Figure 13:
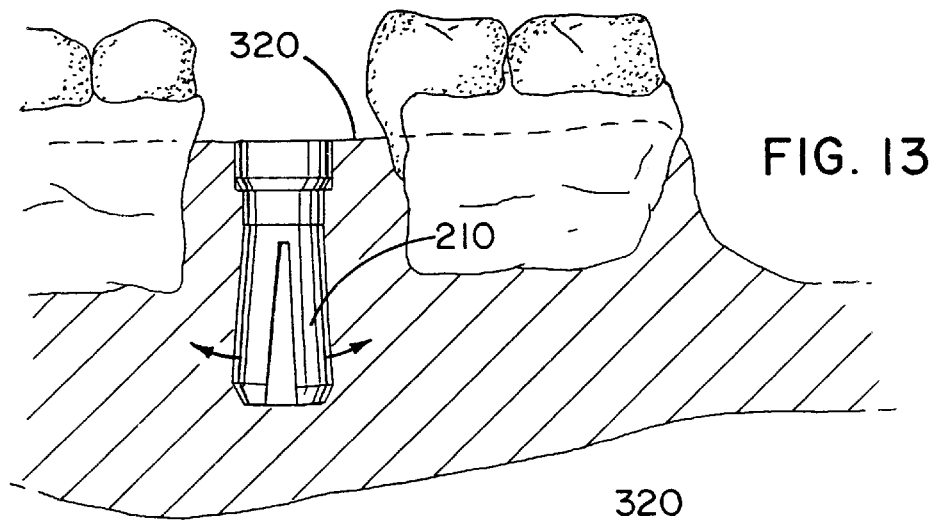
FIG. 13 illustrates a subsequent step of the method of using the implant, showing the legs in an expanded, open position when raised to body temperature.

The legs of the implant 210 self expand from a closed position to an open position when the surgical site warms up, generally within a few moments of being inserted into hole 316 (FIG. 13).

Stability of the implant 210 within the jaw bone is tested using techniques which are generally accepted within dental practice. These include, but are not limited to, applying standardized loads to the implant or by tapping the implant with a metal striker and listening for the sound of a stable implant.

Figure 14:
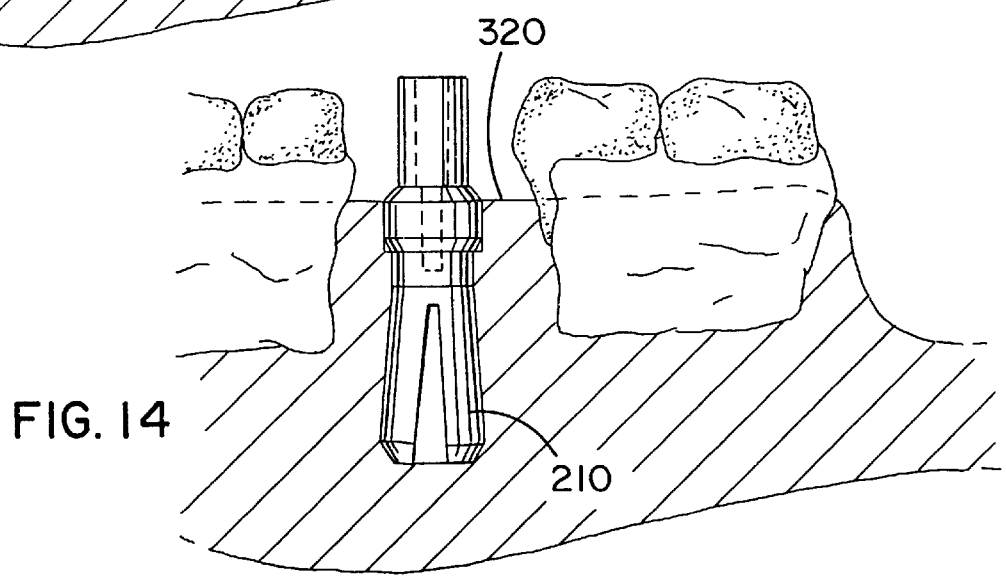
FIG. 14 illustrates a subsequent step of the method of using the implant, showing the abutment attached to the neck of the implant.

If the implant 210 is considered to be stable based upon this test, the abutment is attached to the upper surface of the implant 210 using the screw (FIG. 14). If the implant is not considered to be stable based upon this test, a healing ring is placed over the implant. Further procedures are postponed until stability is achieved. This may take up to six months or more as osseointegration is allowed to proceed.

Figure 15:
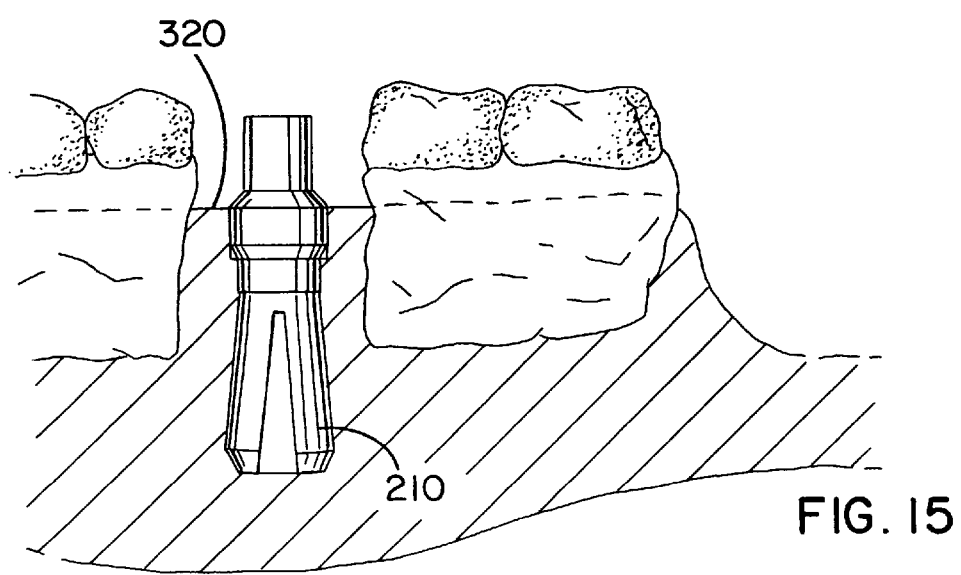
FIG. 15 illustrates a subsequent step of the method of using the implant, showing the shortened abutment portion after trimming.

The abutment is the n trimmed to the appropriate length by removing portions of the upper end of the abutment (FIG. 15). Trimming the abutment is a means to customize its length to the specific requirements of a given procedure. Patients in whom the teeth which surround the implant are small will require more abutment material to be removed than those patients who have larger teeth surrounding the implant site.

Figure 16:
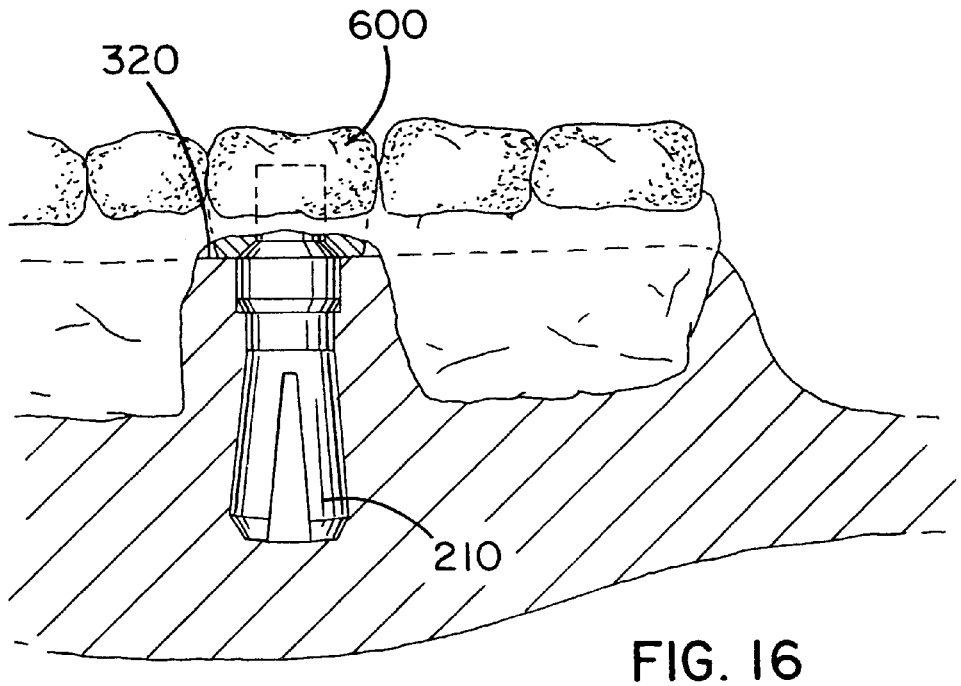
FIG. 16 illustrates a subsequent step of the method of using the implant, showing a crown attached to the abutment portion of the implant.

A temporary or final restoration 600 is attached to the abutment using an adhesive (FIG. 16).

The surgical wound is closed using standard procedures.

Figure 17:
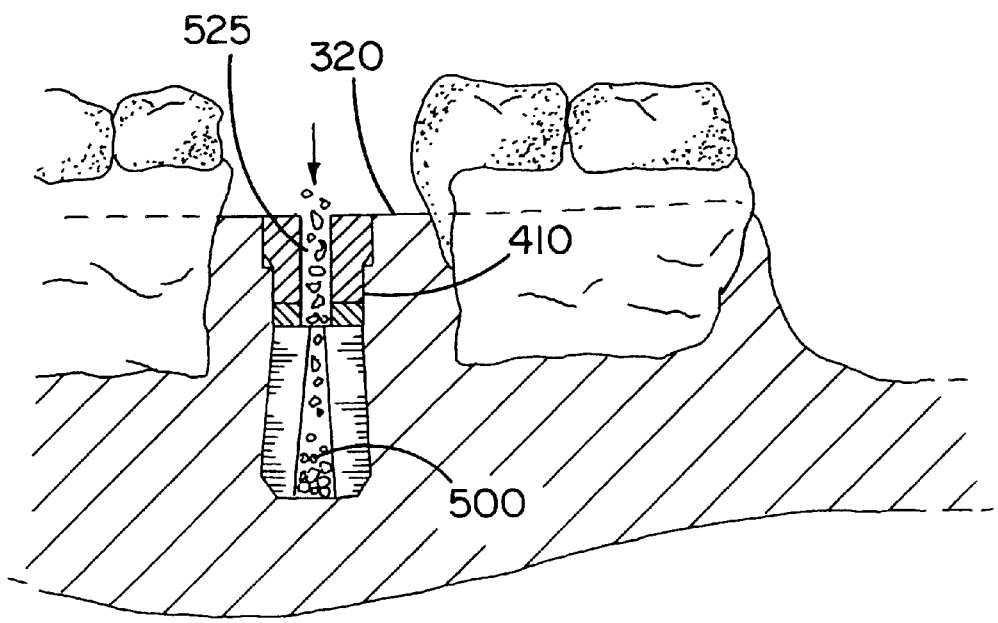
FIG. 17 illustrates a step of the method of using the second embodiment of the implant, showing bone fragments being inserted through the screw channel in order to pack the open space between the legs with bone tissue.

When an implant of the second embodiment 410 is used, an additional method step is inserted following expansion of the legs. In this step, bone fragments 500 are inserted through the channel 525 for placement in the open space between the legs (FIG. 17). This space is packed with bone fragments 500 to promote osseointegration of bone about the implant and provide excellent implant stability. Bone fragments are obtained from the patient's chin or hip bone or the surgeon may elect to use freeze dried demineralized bone or synthetic alloplastic bone, or any suitable alternative.

The above described method of insertion of the implant is an improvement upon previously used methods because of its simplicity. Prior Art implants require additional drilling steps and or the use of bone taps. Additionally, screw drivers or activating tools are required to render the implant stable within the jaw bone. The inventive implant is self expanding, requires very few drilling steps (which reduces the opportunity for heat induced tissue damage), and provides immediate stability.

I claim:

1. A dental implant which provides a structure for receiving a temporary replacement tooth or final restoration, the implant comprising a body portion, a post portion, and means for attaching said post portion to said body portion;

said body portion comprising an elongate cylinder having a longitudinal axis, a first end, a mid portion, and a second end, wherein said body portion has a threaded hole therein, said threaded hole extending from said first end along the longitudinal axis and terminating within said mid portion, and wherein said second end of said body portion comprises at least two elongate legs which extend integrally from said mid portion, said legs having a proximal end and a distal end wherein said proximal ends are joined together to from an apex adjacent said mid portion, and wherein said distal ends can lie in a first position such that the legs are generally closed and lie in a non-spaced, parallel relationship with distal ends substantially adjacent to each other and to the longitudinal axis, and wherein said distal ends can lie in a second position such that the legs are generally open and lie in a fanned out relationship such that the distal ends are substantially spaced apart from each other and spaced away from the longitudinal axis, wherein said post portion comprises an elongate cylinder having a first end and a second end and a smooth, uniform exterior which terminates at a outwardly extending chamfer at said second end, said post portion comprising an axial through channel for receiving said means for attaching said post portion to said body portion, said axial through channel having a uniform diameter from said first end to said second end except adjacent said second end where the diameter is reduced to form an inwardly extending lip portion adjacent said second end of said post portion, wherein said means for attaching said post portion to said body portion comprises a screw having threads sized to be engaged by the threads of the threaded hole of said body portion, and wherein said post portion abuts said body portion in a non-spaced relationship when the implant is assembled.

2. The dental implant of claim 1 wherein the second end of said body portion is comprised of a shape memory material such that when the implant is placed in a cool environment the distal ends of said legs maintain the first position, and when the implant is maintained in a warm environment the distal ends of said legs maintain the second position.

3. The dental implant of claim 2 wherein the first end and mid portion of said body portion is comprised of material which is not affected by temperature.

4. The dental implant of claim 3 wherein the first end of said body portion has a diameter which is larger than the diameter of the mid portion and the second end of said body portion.

5. The dental implant of claim 4 wherein the screw comprises a head portion and a shank portion, wherein the head portion is elongate and has a length such that it completely extends through the axial through channel of the post portion and lies flush with the first end of said post portion, said head portion having an internal hexagonal socket.

6. The dental implant of claim 5 wherein the shape memory material is a Nickel-Titanium alloy.

7. The dental implant of claim 5 wherein the shape memory material is a Titanium-Palladium alloy.

8. The dental implant of claim 5 wherein the shape memory material is a Titanium-Palladium-Cobalt alloy.

9. The dental implant of claim 5 wherein the second end of said body portion comprises four elongate legs.

10. The dental implant of claim 9 wherein the outer aspect of the distal end of each of said legs is rounded.

11. The dental implant of claim 10 wherein the cross section of each leg is shaped like a quarter of a circle such that there are two flat sides at right angles to each other, the two flat sides intersecting at one end and being joined by a smooth circular arc at the other end.

12. A dental implant which provides a structure for receiving a temporary replacement tooth or final restoration, the implant comprising a body portion, a post portion, and means for attaching said post portion to said body portion;

said body portion comprising an elongate cylinder having a longitudinal axis, a first end, a mid portion, and a second end, wherein said second end of said body portion comprises at least two elongate legs which extend integrally from said mid portion, said legs having a proximal end and a distal end wherein said proximal ends are joined together to from an apex adjacent said mid portion, and wherein said distal ends can lie in a first position such that the legs are generally closed and lie in a non-spaced, parallel relationship with distal ends substantially adjacent to each other and to the longitudinal axis, and wherein said distal ends can lie in a second position such that the legs are generally open and lie in a fanned out relationship such that the distal ends are substantially spaced apart from each other and spaced away from the longitudinal axis, wherein said body portion has a longitudinal channel which extends axially from the first end to the second end such that the body portion is generally tubular, said channel having walls which are threaded from the first end to the mid portion, wherein said post portion comprises an elongate cylinder having a first end and a second end and a smooth, uniform exterior which terminates at a outwardly extending chamfer at said second end, said post portion comprising an axial through channel for receiving said means for attaching said post portion to said body portion, said axial through channel having a uniform diameter from said first end to said second end except adjacent said second end where the diameter is reduced to form an inwardly extending lip portion adjacent said second end of said post portion, wherein said means for attaching said post portion to said body portion comprises a screw having threads sized to be engaged by the threads of the channel of said body portion, and wherein said post portion abuts said body portion in a non-spaced relationship when the implant is assembled.

13. The dental implant of claim 12 wherein the second end of said body portion is comprised of a shape memory material such that when the implant is placed in a cold environment the distal ends of said legs maintain the first position, and when the implant is placed in a warm environment the distal ends of said legs maintain the second position.

14. The dental implant of claim 13 wherein the first end and mid portion of said body portion is comprised of material which is not affected by temperature.

15. The dental implant of claim 14 wherein the first end of said body portion has a diameter which is larger than the diameter of the mid portion and the second end of said body portion.

16. The dental implant of claim 15 wherein the screw comprises a head portion and a shank portion, wherein the head portion is elongate and has a length such that it completely extends through the axial through channel of the post portion and lies flush with the first end of said post portion, said head portion having an internal hexagonal socket.

17. The dental implant of claim 16 wherein the shape memory material is a Nickel-Titanium alloy.

18. The dental implant of claim 16 wherein the shape memory material is a Titanium-Palladium alloy.

19. The dental implant of claim 16 wherein the shape memory material is a Titanium-Palladium-Cobalt alloy.

20. The dental implant of claim 16 wherein the second end of said body portion comprises four elongate legs.

21. The dental implant of claim 20 wherein the outer aspect of the distal end of each of said legs is rounded.

22. The dental implant of claim 21 wherein the cross section of each leg is shaped like a quarter of a circle such that there are two flat sides at right angles to each other, the two flat sides intersecting at one end and being joined by a smooth circular arc at the other end.

23. A method of implanting a dental implant in the jaw of a living animal using an implant which is comprised of a body portion, a post portion, and means for attaching said post portion to said body portion;

said body portion comprising an elongate cylinder having a longitudinal axis, a first end, a mid portion, and a second end, wherein said body portion has a threaded hole therein, said threaded hole extending from said first end along the longitudinal axis and terminating within said mid portion, and wherein said first end of said body portion has a diameter which is larger than the diameter of the mid portion and the second end of said body portion, and wherein said second end of said body portion comprises at least two elongate legs which extend integrally from said mid portion, said legs having a proximal end and a distal end wherein said proximal ends are joined together to from an apex adjacent said mid portion, and wherein said distal ends can lie in a first position such that the legs are generally closed and lie in a non-spaced, parallel relationship with distal ends substantially adjacent to each other and to the longitudinal axis, and wherein said distal ends can lie in a second position such that the legs are generally open and lie in a finned out relationship such that the distal ends are substantially spaced apart from each other and spaced away from the longitudinal axis, wherein the second end of said body portion is comprised of a shape memory material such that when the implant is placed in a cool environment the distal ends of said legs maintain said first position, and when the implant is maintained in a warm environment, as found within the body of a living animal, the distal ends of said legs maintain said second position, wherein said post portion comprises an elongate cylinder having a first end and a second end and a smooth uniform exterior which terminates at a outwardly extending chamfer at said second end, said post portion comprising an axial through channel for receiving said means for attaching said post portion to said body portion, said axial through channel having a uniform diameter from said first end to said second end except adjacent said second end where the diameter is reduced to form an inwardly extending lip portion adjacent said second end of said post portion, wherein said means for attaching said post portion to said body portion comprises a screw having threads sized to be engaged by the threads of the threaded hole of said body portion, and wherein said post portion abuts said body portion in a non-spaced relationship when the implant is assembled, the method steps comprising:

1. an implant is provided in non-expanded form by maintaining the implant in a cool environment until implanted;
2. an incision is made in the gun to expose the jaw bone;
3. a first drill is used to verify implant location and direction by forming a small diameter hole we concurrently cooling said hole with a cold water wash to prevent heat-induced tissue damage;
4. a second drill, of larger diameter than the first drill and of the same diameter as the implant, is used to enlarge the hole to final depth and diameter, while concurrently cooling said hole with a cold water wash to prevent heat-induced tissue damage;
5. the upper portion of said hole is enlarged by drilling the upper portion with a counter bore while concurrently cooling with cold water wash to prevent heat-induced tissue damage;
6. the implant is inserted into said hole such that the second end is completely received in said hole and the first end of the body portion of the implant is maintained in a supported relationship in counter bored portion of said hole, while concurrently cooling with a cold water wash to prevent premature expansion of the implant;

7. the cold water wash is discontinued;
8. expansion of legs occurs as the surgical site warms;
9. stability of the implant within the jaw bone is tested;
10. the abutment portion is placed on top of the neck portion of the implant and securely maintained in that position by positioning the screw within the screw channel;
11. the abutment portion is trimmed to an appropriate length;
12. a temporary crown is attached to abutment.

24. The method of claim 23 wherein the screw comprises a head portion and a shank portion, wherein the head portion is elongate and has a length such that it completely extends through the axial through channel of the post portion and lies flush with the first end of said post portion, said head portion having an internal hexagonal socket.

25. The method of claim 24 wherein the shape memory material is a Nickel-Titanium alloy.

26. The method of claim 24 wherein the shape memory material is a Titanium-Palladium alloy.

27. The method of claim 24 wherein the shape memory material is a Titanium-Palladium-Cobalt alloy.

28. The method of claim 24 wherein the second end of said body portion comprises four elongate legs.

29. The method of claim 28 wherein the outer aspect of the distal end of each of said legs is rounded.

30. The method of claim 29 wherein the cross section of each leg is shaped like a quarter of a circle such that there are two flat sides at right angles to each other, the two flat sides intersecting at one end and being joined by a smooth circular arc at the other end.

31. A method of implanting a dental implant in the jaw of a living animal using an implant which is comprised of a body portion, a post portion, and means for attaching said post portion to said body portion;

said body portion comprising an elongate cylinder having a longitudinal axis, a first end, a mid portion, and a second end, wherein said second end of said body portion comprises at least two elongate legs which extend integrally from said mid portion, said legs having a proximal end and a distal end wherein said proximal ends are joined together to from an apex adjacent said mid portion, and wherein said distal ends can lie in a first position such that the legs are generally closed and lie in a non-spaced, parallel relationship with distal ends substantially adjacent to each other and to the longitudinal axis, and wherein said distal ends can lie in a second position such that the legs are generally open and lie in a fanned out relationship such that the distal ends are substantially spaced apart from each other and spaced away from the longitudinal axis, wherein the second end of said body portion is comprised of a shape memory material such that when the implant is placed in a cool environment the distal ends of said legs maintain said first position, and when the implant is maintained in a warm environment, as found within the body of a living animal, the distal ends of said legs maintain said second position, wherein said body portion has a longitudinal channel which extends axially from the first end to the the second end such that the body portion is tubular, said channel having walls which are threaded from the first end to the mid portion, wherein said first end of said body portion has a diameter which is larger than the diameter of the mid portion and the second end of said body portion, and wherein said post portion comprises an elongate cylinder having a first end and a second end and a smooth, uniform exterior which terminates at a outwardly extending chamfer at said second end, said post portion comprising an axial through channel for receiving said means for attaching said post portion to said body portion, said axial through channel having a uniform diameter from said first end to said second end except adjacent said second end where the diameter is reduced to form an inwardly extending lip portion adjacent said second end of said post portion, wherein said means for attaching said post portion to said body portion comprises a screw having threads sized to be engaged by the threads of the channel of said body portion, and wherein said post portion abuts said body portion in a non-spaced relationship when the implant is assembled. the method steps comprising:

1. an implant is provided in non-expanded form by maintaining the implant in a cool environment until implanted;
2. an incision is made in the gum to expose the jaw bone
3. a first drill is used to verify implant location and direction by forming a small diameter hole while concurrently cooling said bole with a cold water wash to prevent heat-induced tissue damage;
4. a second drill, of larger diameter than the first drill and of the same diameter as the implant, is used to enlarge the hole to final depth and diameter, while concurrently cooling said hole with a cold water wash to prevent heat-induced tissue damage;
5. the upper portion of said hole is enlarged by drilling the upper portion with a counter bore while concurrently cooling with cold water wash to prevent heat-induced tissue damage;
6. the implant is inserted into said hole such that the legs are completely received in said hole and the neck portion of the implant is maintained in a supported relationship in counter bored portion of said hole, while concurrently cooling with a cold water wash to prevent premature expansion of the implant;
7. the cold water wash is discontinued;
8. expansion of legs occurs as surgical site warms;
9. bone fragments are inserted through the screw channel into the open space between the expanded legs;
10. stability of the implant within the jaw bone is tested;
11. the abutment portion is placed on top of the neck portion of the implant and securely maintained in that position by positioning the screw within the screw channel;
12. the abutment portion is trimmed to an appropriate length;
13. a temporary crown is attached to abutment.

32. The method of claim 31 wherein the screw comprises a head portion and a shank portion, wherein the head portion is elongate and has a length such that it completely extends through the axial through channel of the post portion and lies flush with the first end of said post portion, said head portion having an internal hexagonal socket.

33. The method of claim 32 wherein the shape memory material is a Nickel-Titanium alloy.

34. The method of claim 32 wherein the shape memory material is a Titanium-Palladium alloy.

35. The method of claim 32 wherein the shape memory material is a Titanium-Palladium-Cobalt alloy.

36. The method of claim 32 wherein the second end of said body portion comprises four elongate legs.

37. The method of claim 36 wherein the outer aspect of the distal end of each of said legs is rounded.

38. The method of claim 37 wherein the cross section of each leg is shaped like a quarter of a circle such that there are two flat sides at right angles to each other, the two flat sides intersecting at one end and being joined by a smooth circular arc at the other end.

39. A dental implant having an upper portion and a lower portion, said upper portion comprised of a biocompatible material which is unaffected by surrounding temperatures, and said lower portion comprised of a biocompatible material which is sensitive to temperature, the upper portion comprised of a post, a body, and attachment means, said post having a first end and a second end, the second end of said post abutting the body in a non-spaced relationship when fixed to said body via the attachment means, herein said attachment means comprises a bore extending through the post from the first end to the second end, said bore having a uniform diameter except immediately adjacent the second end of the post where the diameter is reduced to form an inwardly extending lip within the bore, the attachment means further comprising a screw having an elongate head, said head abutting said lip and extending through said bore such that the head lies flush with the first end of the post.

40. The dental implant of claim 39 wherein said lower portion is comprised of a biocompatible material which has the property wherein the lower portion assumes a first shape at a first temperature and assumes a second shape at a second temperature.

41. The dental implant of claim 40 wherein the implant is comprised of an elongate cylindrical body wherein said upper portion is comprised of an abutment shaped to receive a replacement tooth thereon and a neck which is of larger diameter than the abutment and lies adjacent the abutment, and wherein said lower portion is comprised of at least two self expanding legs.

42. The dental implant of claim 41 wherein said first shape comprises the legs in a non-expanded conformation, and wherein said second shaped comprises the legs in an expanded conformation.

43. The dental implant of claim 42 wherein said second temperature is a warm temperature such as generally found in the body of an animal and wherein said first temperature is a cold temperature such as generally found in an ice water bath.

44. A dental implant which provides a structure for receiving a temporary replacement tooth or final restoration, the implant comprising a body portion, a post portion, and means for attaching said post portion to said body portion;

said body portion comprising an elongate cylinder having a longitudinal axis, a first end, a mid portion, and a second end, wherein said second end of said body portion comprises at least two elongate legs which extend integrally from said mid portion, said legs having a proximal end and a distal end wherein said proximal ends are joined together to from an apex adjacent said mid portion, and wherein said distal ends can lie in a first position such that the legs are generally closed and lie in a non-spaced, parallel relationship with distal ends substantially adjacent to each other and to the longitudinal axis, and wherein said distal ends can lie in a second position such that the legs are generally open and lie in a fanned out relationship such that the distal ends are substantially spaced apart from each other and spaced away from the longitudinal axis, wherein the second end of said body portion is comprised of a shape memory material such that when the implant is placed in a cold environment the distal ends of said legs maintain the first position, and when the implant is placed in a warm environment the distal ends of said legs maintain the second position, wherein the first end and mid portion of said body portion are comprised of a material which is not sensitive to temperature, wherein said body portion has a longitudinal channel which extends axially from the first end to the second end such that a passageway is formed between the first and second ends of the body portion, said channel comprising a first portion which lies within said first end and mid portion of said body portion, is threaded, and thus is formed of material which is not temperature sensitive, said channel comprising a second portion which lies within said second end of said body portion and thus is formed of said shape memory material, wherein said post portion comprises an elongate cylinder having a first end and a second end and a smooth, uniform exterior which terminates at a outwardly extending chamfer at said second end, said post portion comprising an axial through channel for receiving said means for attaching said post portion to said body portion, said axial through channel having a uniform diameter from said first end to said second end except adjacent said second and where the diameter is reduced to form an inwardly extending lip portion adjacent said second end of said post portion, wherein said means for attaching said post portion to said body portion comprises a screw having threads sized to be engaged by the threads of the channel of said body portion, wherein said post portion abuts said body portion in a non-spaced relationship when the implant is assembled, and wherein the post portion and said screw are from a material which is not temperature sensitive.

* * * * *